(12) United States Patent
Mainprize et al.

(10) Patent No.: US 10,595,805 B2
(45) Date of Patent: Mar. 24, 2020

(54) SYSTEMS AND METHODS FOR GENERATING AN IMAGING BIOMARKER THAT INDICATES DETECTABILITY OF CONSPICUITY OF LESIONS IN A MAMMOGRAPHIC IMAGE

(71) Applicant: SUNNYBROOK RESEARCH INSTITUTE, Toronto, Ontario (CA)

(72) Inventors: James Mainprize, Toronto (CA); Olivier Alonzo-Proulx, Toronto (CA); Martin Yaffe, Toronto (CA); Gordon Mawdsley, Toronto (CA)

(73) Assignee: Sunnybrook Research Institute, Toronto (CA)

( * ) Notice: Subject to any disclaimer, the term of this patent is extended or adjusted under 35 U.S.C. 154(b) by 391 days.

(21) Appl. No.: 15/321,525

(22) PCT Filed: Jun. 26, 2015

(86) PCT No.: PCT/CA2015/050602
§ 371 (c)(1),
(2) Date: Dec. 22, 2016

(87) PCT Pub. No.: WO2015/196300
PCT Pub. Date: Dec. 30, 2015

(65) Prior Publication Data
US 2017/0202530 A1 Jul. 20, 2017

Related U.S. Application Data

(60) Provisional application No. 62/018,335, filed on Jun. 27, 2014.

(51) Int. Cl.
*A61B 6/00* (2006.01)
*A61B 6/12* (2006.01)
(Continued)

(52) U.S. Cl.
CPC .............. *A61B 6/502* (2013.01); *A61B 6/032* (2013.01); *A61B 6/12* (2013.01); *A61B 6/461* (2013.01);
(Continued)

(58) Field of Classification Search
None
See application file for complete search history.

(56) References Cited

U.S. PATENT DOCUMENTS 5,657,362 A * 8/1997 Giger ................... G06T 7/0012
378/37
6,137,904 A 10/2000 Lubin
(Continued)

FOREIGN PATENT DOCUMENTS

CA 2438479 3/2004
WO 2000005677 2/2000
(Continued)

OTHER PUBLICATIONS

Alonzo-Proulx, O., et al. "Validation of a method for measuring the volumetric breast density from digital mammograms." Physics in Medicine & Biology 55.11 (2010): 3027.
(Continued)

*Primary Examiner* — Brian T Gedeon
(74) *Attorney, Agent, or Firm* — Quarles & Brady LLP

(57) ABSTRACT

Systems and methods for generating imaging biomarkers that indicate detectability or conspicuity of lesions that may be present in mammographic images are provided. In general, a task-based measure of a signal-to-noise ratio ("SNR") measurement of a detection task is computed over a number of small regions-of-interest ("ROIs") in an image, and the computed parameter is used to predict what detection rates should be if a lesion was present in the image. As such, the computed parameter can be used to define an imaging
(Continued)

biomarker that is a "masking measure" that indicates the degree of conspicuity of lesions that may be present in a given a mammographic image.

29 Claims, 8 Drawing Sheets

(51) Int. Cl.
*A61B 6/03* (2006.01)
*G06F 19/00* (2018.01)

(52) U.S. Cl.
CPC .............. *A61B 6/469* (2013.01); *A61B 6/481* (2013.01); *G06F 19/321* (2013.01)

(56) References Cited

U.S. PATENT DOCUMENTS

| | | | |
|---|---|---|---|
| 6,246,782 | B1 | 6/2001 | Shapiro |
| 6,748,044 | B2 | 6/2004 | Sabol |
| 6,819,790 | B2 | 11/2004 | Suzuki |
| 8,090,177 | B2 | 1/2012 | Venkataraman |
| 8,315,446 | B2 | 11/2012 | Raundahl |
| 8,340,388 | B2 | 12/2012 | Rosenstengel |
| 8,494,227 | B2 | 7/2013 | Prokoski |
| 8,543,519 | B2 | 9/2013 | Guyon |
| 8,582,858 | B2 | 11/2013 | Su |
| 8,594,410 | B2 * | 11/2013 | Schmidt .............. G06K 9/6253 382/128 |
| 8,687,860 | B2 | 4/2014 | Gustafson |
| 8,698,087 | B2 | 4/2014 | Surti |
| 8,712,157 | B2 | 4/2014 | Marchesotti |
| 8,731,291 | B2 | 5/2014 | Hao |
| 8,923,594 | B2 | 12/2014 | Wehnes |
| 8,977,019 | B2 | 3/2015 | Chan |
| 2005/0041844 | A1 | 2/2005 | Yamanaka |
| 2005/0283076 | A1 * | 12/2005 | Hangiandreou ..... A61B 8/0825 600/443 |
| 2009/0082637 | A1 | 3/2009 | Galperin |
| 2013/0343626 | A1 | 12/2013 | Rico |
| 2014/0072108 | A1 * | 3/2014 | Rohler .................. A61B 6/482 378/207 |

FOREIGN PATENT DOCUMENTS

| | | |
|---|---|---|
| WO | 2003087983 | 10/2003 |
| WO | 2010014068 | 2/2010 |
| WO | 2011087807 | 7/2011 |
| WO | 2011100511 | 8/2011 |

OTHER PUBLICATIONS

Baydush, Alan H., et al. "Computer aided detection of masses in mammography using subregion Hotelling observers." Medical Physics 30.7 (2003): 1781-1787.

Bochud, F. O. et al. "Statistical texture synthesis of mammographic images with clustered lumpy backgrounds." Optics express 4.1 (1999): 33-43.

Boone, J.M., Cooper, V.N.: Scatter/primary in mammography: Monte Carlo validation. Med. Phys. 27, 1818-1831 (2000).

Boyd, et al., in "Mammographic density and the risk and detection of breast cancer," N Engl J Med., 2007; 356(3):227-236.

Boyd, N.F., et al.: Mammographic densities as a marker of human breast cancer risk and their use in chemoprevention. Curr. Oncol. Rep. 3, 314-21 (2001).

Burgess, et al. "Human observer detection experiments with mammograms and power-law noise," Med. Phys., 2001; 28(4):419-437).

Byng, J. W., et al. "Automated analysis of mammographic densities." Physics in Medicine & Biology 41.5 (1996): 909.

Byng, J.W., et al.: Analysis of mammographic density and breast cancer risk from digitized mammograms. Radiographics. 18, 1587-98 (1998).

Cahill, C. J., et al. "Features of mammographically negative breast tumours." British Journal of Surgery 68.12 (1981): 882-884.

Caldwell, Curtis B., et al. "Characterisation of mammographic parenchymal pattern by fractal dimension." Physics in medicine & biology 35.2 (1990): 235.

Carney, P.A., et al.: Individual and combined effects of age, breast density, and hormone replacement therapy use on the accuracy of screening mammography. Ann. Intern. Med. 138, 168-175 (2003).

Gong, Xing, et al. "A computer simulation study comparing lesion detection accuracy with digital mammography, breast tomosynthesis, and cone-beam CT breast imaging." Medical physics 33.4 (2006): 1041-1052.

International Search Report for application PCT/CA2015/050602, dated Oct. 5, 2015, 9 pages.

Ma, L., et al. "Case-control study of factors associated with failure to detect breast cancer by mammography." JNCI: Journal of the National Cancer Institute 84.10 (1992): 781-785.

Mainprize, J.G., Yaffe, M.J.: Cascaded analysis of signal and noise propagation through a heterogeneous breast model. Med. Phys. 37, 5243-5250 (2010).

Mandelson, Margaret T., et al. "Breast density as a predictor of mammographic detection: comparison of interval-and screen-detected cancers" Journal of the National Cancer Institute 92.13 (2000): 1081-1087.

Porter, Peggy L., et al. "Breast tumor characteristics as predictors of mammographic detection: comparison of interval- and screen-detected cancers." Journal of the National Cancer Institute 91.23 (1999): 2020-2028.

Reiser, I., et al.: On the orientation of mammographic structure. Med. Phys. 38, 5303-5306 (2011).

Samei, E., et al.: A method for measuring the presampled MTF of digital radiographic systems using an edge test device. Med. Phys. 25, 102-113 (1998).

Saunders, Robert S., et al. "Does image quality matter? Impact of resolution and noise on mammographic task performance" Medical physics 34.10 (2007): 3971-3981.

Van Gils, Carla H., et al. "Mammographic breast density and risk of breast cancer: masking bias or causality?." European journal of epidemiology 14.4 (1998): 315-320.

* cited by examiner

SYSTEMS AND METHODS FOR GENERATING AN IMAGING BIOMARKER THAT INDICATES DETECTABILITY OF CONSPICUITY OF LESIONS IN A MAMMOGRAPHIC IMAGE

CROSS-REFERENCE TO RELATED APPLICATIONS

This application represents the national stage entry of PCT International Application PCT/CA2015/050602 filed Jun. 26, 2015, which claims the benefit of U.S. Provisional Application 62/018,335 filed Jun. 27, 2014. The contents of this application are hereby incorporated by reference as if set forth in their entirety herein.

BACKGROUND OF THE INVENTION

The field of the invention is systems and methods for x-ray mammography. More particularly, the invention relates to systems and methods for estimating the degree of difficulty of finding a lesion within a mammographic image, such as an image acquired with digital mammography, digital tomosynthesis, dual-energy mammography, or contrast-enhanced mammography.

Women presenting with mammographically dense breasts have increased risk of developing breast cancer, and screening mammography has been shown to have reduced sensitivity for dense breasts. While there is considerable interest in quantification of mammographic density, little attention has been directed at developing an index that reflects the "difficulty" of interpreting a mammographic image related to that density.

Mammographic density describes the amount of "fibroglandular tissue," either on an absolute or relative scale, to the total amount of breast tissue. Fibroglandular tissue is a term used to describe the fibrous (stroma) and glandular (epithelial or parenchymal) tissue components. Other tissues, such as blood vessels, skin, and ligaments also contribute to the radiographic density of breast tissue. The non-dense tissue is largely adipose tissue. In mammography, the fibroglandular (i.e., dense) tissue attenuates x-ray intensities more strongly than adipose tissue, resulting in areas of "density" typically displayed as whiter than the fatty background.

Mammography has reduced accuracy for dense breasts because the lesion has reduced contrast in dense tissue and is thus harder to see. Another reason that mammography has reduced accuracy for dense breasts is because the background tissue structure or "texture" is distracting and thereby causes the lesions to become less conspicuous. This texture is noticeably more apparent in mid- and high-density breasts. Also, mammographic breast density has been identified as an independent risk factor for breast cancer, and studies have identified a 4-5 fold increase in risk for developing breast cancer in women with dense breast tissue versus women with very little dense breast tissue (i.e., breast tissue with more fat), as described by N. F. Boyd, et al., in "Mammographic density and the risk and detection of breast cancer," *N Engl J Med.*, 2007; 356(3):227-236.

The addition of breast density quantification to mammographic examination has the potential to greatly improve the accuracy of breast cancer risk assessment, especially for those without hereditary or familial risk factors. The inclusion of accurate breast density measurements and masking characteristics can also be potentially helpful for women already determined to be at high risk for breast cancer, for instance, by suggesting that other imaging modalities such as magnetic resonance imaging ("MRI") or ultrasound be used for initial screening instead of mammography because mammography's accuracy is known to be reduced in women with very dense breasts.

Because the reporting of breast density is required in some jurisdictions, there is a desire to provide an accurate and reproducible quantitative density measurement method that is simple to implement on conventional digital mammography machines. Nevertheless, breast density alone is not a measure of the "difficulty" of a mammographic image. Other factors such as texture, image noise, and x-ray technique factors may affect lesion conspicuity. Lesion "masking" is therefore a result of several parameters that reduce the conspicuity of a lesion. In other words, masking results in the lesion being harder to see in the image.

The current standard of reporting the density of a mammographic image is performed by radiologists in assigning a qualitative Breast Imaging-Reporting and Data System ("BIRADS") density score (a-d), with "a" being a largely fatty breast, and "d" being a very dense breast. This assessment gives a basic indication of the difficulty of the detection of cancer in that image.

In a recent study, A. E. Burgess, et al. ("Human observer detection experiments with mammographic images and power-law noise," *Med. Phys.*, 2001; 28(4):419-437), describe a method for using model observers to estimate a measure of lesion masking. In this study, a series of regions-of-interest are extracted from a series of mammographic images, and "simulated" lesions are synthetically added to each ROI. These simulated images are then used in a carefully controlled reader study (called an Alternative-Forced Choice study) to validate the model observers that were used. The study attempted to determine the model observers that best match the humans that participated in the reader study; however, the Burgess study does not otherwise provide a measurement of the difficulty of detecting lesions in a particular mammographic image.

SUMMARY OF THE INVENTION

The present invention overcomes the aforementioned drawbacks by providing a method for generating an imaging biomarker that indicates a degree of detectability for lesions that may be present in a mammographic image obtained with an x-ray imaging system. A mammographic image acquired with an x-ray imaging system is provided and the mammographic image is processed to estimate a task-based measure that is based on a statistical measure of a detection task. An imaging biomarker that indicates a degree of lesion detectability for lesions that may be present in the mammographic image is generated based on the estimated task-based measure. A report that indicates the degree of lesion detectability in the mammographic image is generated based on the imaging biomarker.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
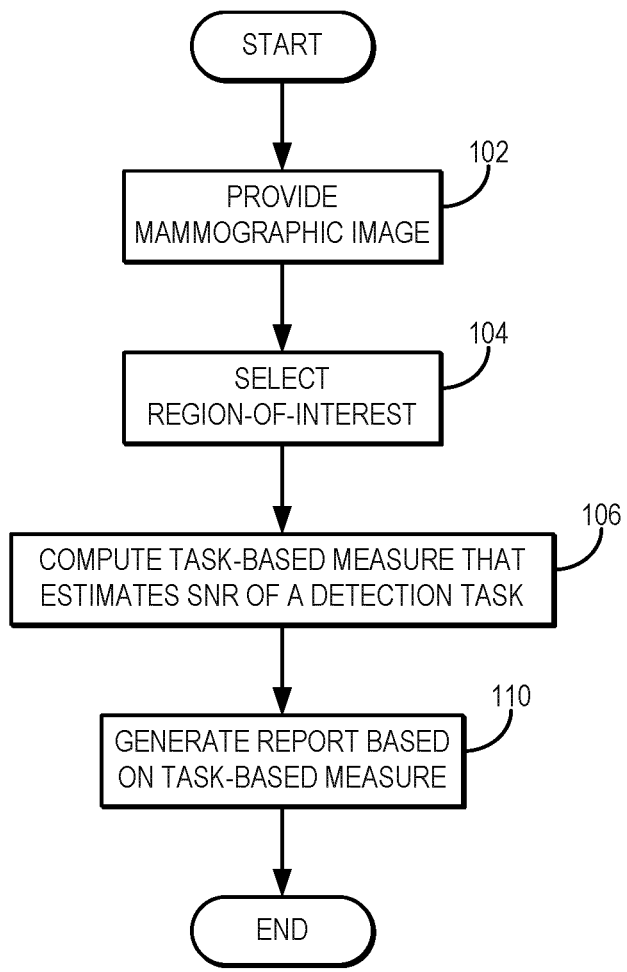
FIG. 1 is a flowchart setting forth the steps of an example method for generating an imaging biomarker that indicates lesion detectability, conspicuity, or masking in a mammographic image.

Described here are systems and methods for generating imaging biomarkers that indicate detectability of lesions that may be present in mammographic images. That is, the imaging biomarkers indicate the degree of difficulty for a detection task of detecting whether lesions may be present in a particular mammographic image, or region-of-interest in a mammographic image, without out actually identifying the presence of such lesions. In general, the systems and methods include computing a signal-to-noise ratio ("SNR") measurement over a number of small regions-of-interest ("ROIs") in an image, and the computed parameter is used to predict what detection rates would be if a lesion was present in the image. As such, the computed parameter can be used to define an imaging biomarker that is a "masking measure" that indicates the degree of conspicuity of potential lesions that may be present in a given a mammographic image. Thus, in general, as the estimated conspicuity decreases, the masking measure increases. These systems and methods can thus be used to inform a clinician whether a particular mammographic image would be suitable for detecting an actual lesion, or whether alternative screening methods should be utilized to achieve more reliable diagnostic results.

As used herein, the term "mammographic image" refers to an image generated from at least one x-ray projection image that is reconstructed for display as a single image or series of images. Mammographic images may be obtained using any one of standard digital mammography, digital tomosynthesis, dual-energy mammography, or contrast-enhanced mammography.

The systems and methods of the present invention utilize a task-based measure of potential lesion conspicuity. Conspicuity is calculated on an array of small ROIs as if a lesion of a particular size and shape were actually embedded in the tissue. In some embodiments, the imaging biomarker measure may be obtained directly from measurements of the image properties. Examples of image properties that can be used to compute the imaging biomarker include image noise power spectra and texture measures, such as the fractal dimension or an "inverse-power law" coefficient that corresponds to the slope of the image power spectrum.

In some other embodiments, the imaging biomarker measure may be extracted from a physical model that uses coefficients and parameters that are either extracted from the image itself, or are recorded in the DICOM header of the image. The model approach can potentially be more useful because the model is less prone to measurement errors in obtaining the parameters from each ROI. Additionally, the model may be used as a robust method to compare lesion conspicuity to various parameters associated with the image.

The systems and methods of the present invention can provide a "scoring map" based on the generated imaging biomarker, whereby the scoring map indicates areas that are expected to be difficult to detect cancer based on tissue density and texture. Although there are a number of algorithms that predict tissue density, none to date have attempted to extract a measure of the expected lesion conspicuity. This measure of the expected lesion conspicuity, which may be referred to as a "masking score," may be useful in determining those women who should be recommended for alternative screening modalities. The masking score may also be used to flag images for additional review and closer scrutiny by a panel of radiologists, and may also be useful for directing computer-aided detection algorithms.

The systems and methods described here can be used on images from any mammography system with a minimal set of information for each acquisition workstation. As an example, the methods described here can be implemented on a computer workstation in a radiology department. The ability to objectively identify those mammographic images in which it will be more difficult to detect lesions will be informative to the radiologist and may be used to identify women who should be invited to have alternative breast cancer screening strategies.

Mammographic imaging errors (i.e., where lesions go undetected following image analysis) may be due to any one or more of a number of different reasons. Example of these reasons include the following:

(1) "Detection error," which is generally defined as an error that occurs when an existing lesion is not identified upon radiological examination. Such errors may be due to lack of practitioner skill; fatigue; "satisfaction of search" error (i.e., one detected the larger lesion, but is unable to identify a smaller, inconspicuous lesion); and masking effects, where masking may be due to reduction in lesion conspicuity due to extent of surrounding normal fibroglandular tissue.

(2) "Interpretation error," which is generally defined as a misclassification error following lesion detection. Such errors may result in miscategorization of a lesion, such as mischaracterizing a benign lesion as malignant or mischaracterizing a malignant lesion as benign. Interpretation errors arise from incomplete information (e.g., the lesion was found only in one view or was not detectable by alternative screening methods, such as ultrasound), exhibition of features by an abnormality/lesion more commonly associated with benign lesions, or due to apparent stability of the lesion upon comparison to earlier images.

As indicated above, interpretation errors can be reduced with increased radiological experience, the inclusion of second reader opinion, improved image quality, and improved image positioning. By definition, interpretation errors occur when the lesion is visible on the image and, in theory, could be eliminated if sufficient resources were applied to mitigate the error.

As used herein, the term "masking" is defined as the obscuring or partial obscuring of a lesion by surrounding normal fibroglandular tissue resulting in the lesion going undetected by the practitioner reader. The conspicuity of a lesion is dependent on a number of different factors, including the relative contrast or signal difference between the lesion and the nearby background in the image, and the complexity of the background structures that may distract or confound the reader's examination of the image for a lesion.

As used herein, the term "sensitivity" is defined as the ratio of the number of images or examinations identified by the imaging test (e.g., by mammography or tomosynthesis imaging) as containing malignant abnormalities in a population or test set compared to the actual number of images or examinations containing malignancies in that population. This can be calculated as the number of "true positives" divided by the total number of positive images or examinations (true positives plus false negatives).

As used herein, the term "specificity" is defined as the ratio of the number of images or examinations correctly identified as normal by the imaging test (true negatives) to the total number of images or examinations in the population or test set where the disease is not present. This can be calculated as the number of true negatives divided by the sum of the true negatives and the false positives.

Task-based measures of lesion conspicuity often use a measure of signal-to-noise ratio that can be defined as follows:

$$d' = \frac{\bar{t}_1 - \bar{t}_0}{\sqrt{\sigma_1^2 + \sigma_0^2}}; \tag{1}$$

where $\bar{t}_1$ is the average result of a test statistic when a lesion is present, $\bar{t}_0$ is the average result of the test statistic when a lesion is absent, and $\sigma_1^2$ and $\sigma_0^2$ are the respective variances of these test statistics. Tasks may include detection (e.g., lesion present, lesion not present), discrimination (e.g., lesion malignant, lesion benign), or estimation (e.g., lesion size). Tasks may be simple (lesion shape and location is known, if present) or complex (location unknown, lesion shape unknown).

In the case of missed lesions for mammography, the task that is of concern is that of lesion detection. To calculate the true d' for any given mammographic image, in which the task includes a "search and scan component" and multiple lesion possibilities, would be significantly difficult. To address this drawback, a surrogate measure referred to as "local detectability" is introduced, represented by the symbol, $d_{local}$, which is a measure of a simple detection task of a single object in a small ROI in the mammographic image. The $d_{local}$ measure is expected to be reasonably proportional to a real lesion detection task, but not as an absolute scale. Lesion masking is expected to occur when $d_{local}$ is very low. This parameter can be calculated on adjacent or overlapping small ROIs (e.g. ROIs of 32×32 pixels, 256×256 pixels).

The linearity of pixel values reported by modern FFDM systems in arbitrary digital units ("ADU") per mAs is very stable. An mAs-normalized arbitrary digital unit ("NADU") is defined here to be the mean pixel value of a region-of-interest ("ROI") normalized by the mAs for the unprocessed ("RAW") digital image.

When only air is imaged the NADU value is designated as $NADU_{air}$. For a given target, filter, kV, and thickness combination, the attenuation, $\alpha$, can be defined as, $$\alpha = \frac{NADU}{NADU_{air}}. \tag{2}$$

Logarithmic attenuation can thus be defined as, $$LA = \log_{10}(\alpha) = \log_{10}\left(\frac{NADU}{NADU_{air}}\right). \tag{3}$$

In logarithmic space, the logarithmic attenuation of breast tissue is linear with respect to percentage of fibroglandular tissue. The logarithmic attenuation is useful for the VBD estimation and for extracting image parameters that are largely independent of the x-ray exposure.

The $d_{local}$ parameter is calculated based on assumptions about the observer, which could be represented by various "model observers," which include but are not limited to: pre-whitening, non-prewhitening, Hotelling and, channelized Hotelling model observers. Each of these model observers could be expanded to include "human" parameters that add model parameters for the human visual system and human decision making. These model observers may be applied directly to images or to the Fourier spectrum of the images. An example of such a calculation is for the non-prewhitening model observer in the Fourier domain is:

$$d_{local}^2 = \frac{\left[\int T^2(u,v)W^2(u,v)dudv\right]^2}{\int NNPS(u,v)T^2(u,v)W^2(u,v)dudv}; \tag{4}$$

where (u,v) are spatial frequencies in the x-direction and y-direction, respectively; T(u,v) is the modulation transfer function ("MTF") of the imaging system; W(u,v) is the task function (e.g., the function that describes a particular detection task); and NNPS(u,v) is the normalized noise power spectrum. As an alternative to using the MTF, other resolution-based measures of the imaging system can also be suitably used when computing the task-based measure. For instance, the point spread function ("PSF") could also be used.

As one non-limiting example, the task function, W(u,v) can be selected based on the detection of a uniform disk of a certain radius, $$W(\rho) = \frac{CRJ_1(2\pi R\rho)}{\rho};\quad(5)$$

where $\rho$ is the radial spatial frequency, $J_1(\rho)$ is the Bessel function of the first kind and C is the object signal difference ("contrast"), which can be assumed to be, $$C \approx \Delta\mu L \quad(6)$$

where $\Delta\mu$ is the difference in linear attenuation between lesion and adipose tissue and L is the thickness of the simulated lesion, which in this example is L=2R. As an example, the radius can be selected as R=2.5 mm.

In general, the lesion shape incorporated into the task function $W(u,v)$ may be any reasonable shape and size that might be appropriate for mammographic image. A non-limiting example may be a uniform disc of with a radius of 2.5 mm, as mentioned above, which represents a small, sharp lesion. Another example may be a lesion represented by a Gaussian profile with softer edges.

One parameter that can significantly affect lesion conspicuity is the appearance of the mammographic background tissue. Mammographic images in particular have shown power spectra associated with fibroglandular texture or "anatomic noise" to have the form, $$S_a(\rho) = \frac{K}{\left(1 + \frac{\rho}{f_0}\right)^\beta};\quad(7)$$

where K is a scale factor related to the signal difference between fat and fibroglandular tissue, $\beta$ is the estimated power-law spectrum exponent extracted from the ROI, and $f_0$ is a constant that provides a stable equation at low spatial frequencies. As one example, $f_0$ can be selected as $f_0=0.1$ mm$^{-1}$.

In some embodiments, the NNPS can be extracted directly from each ROI; however, it is contemplated that such an approach would result in high variability in the $d_{local}$ values. Thus, in some embodiments, NNPS can also be estimated based on a simple model of x-ray propagation through simulated tissue. An example of such a model may have the form, $$NNPS_0(P) = \frac{\Phi_p + \Phi_s + \Phi_p^2 S_a(\rho)}{(\Phi_p + \Phi_s)^2} = \frac{1}{\Phi_p + \Phi_s} + \frac{S_a(\rho)}{\left(1 + \frac{\Phi_s}{\Phi_p}\right)^2};\quad(8)$$

where $\Phi_p$ and $\Phi_s$ are the absorbed fluences in the detector due to the primary and scattered x-rays, respectively. The absorbed fluences can include the effects of an antiscatter grid and quantum efficiency, which can be assumed to be the same for both $\Phi_p$ and $\Phi_s$. Average primary transmission can be estimated from the calculated thickness and volumetric breast density ("VBD"), and the x-ray parameters extracted from the DICOM header of the image file (e.g. kV, mAs). Scatter can be measured or estimated using a model, such by using a scatter point spread function similar to the one described by J. M. Boone and V. N. Cooper in "Scatter/primary in mammography: Monte Carlo validation," *Med. Phys.*, 2000; 27:1818-1831, knowing the thickness and composition of the breast.

To ensure fidelity of the model to the actual image, the model result for the NNPS can be scaled to an overall measure of the measured NNPS. For instance, the NNPS can be scaled over a spatial frequency range in which the measured NNPS is expected to be reasonably stable. As an example, the modeled NNPS can be rescaled according to, $$NNPS(u,v) = m \cdot NNPS_0(u,v) \quad(9);$$

where $$m = \frac{\int_{f_1}^{f_2} NNPS_{measured}(\rho\cos\theta, \rho\sin\theta)\rho d\rho}{\int_{f_1}^{f_2} NNPS_0(\rho)\rho d\rho};\quad(10)$$

where $(f_1, f_2)$ denotes the region of the NNPS that is assumed to be dominated by quantum noise rather than the anatomic component, and is therefore likely to be relatively stable between measurements. As an example, $f_1$ may be 4 mm$^{-1}$ and $f_2$ may be 5 mm$^{-1}$.

The model for the NNPS incorporates both the quantum noise effects related to the incident x-ray exposure, the x-ray transmission through the breast and the mammographic texture as modeled by the inverse power law spectrum equation and its $\beta$ factor. Thus, $d_{local}$ is sensitive to breast density and to the general texture of the mammographic background.

Referring now to FIG. 1, a flowchart is shown setting forth the steps of an example method for generating an imaging biomarker that indicates the degree of lesion conspicuity in a mammographic image. For instance, the method generates an imaging biomarker that indicates a degree of lesion masking in a mammographic image, where the lesion masking is caused by breast density and tissue patterns.

The method includes providing one or more images acquired with a mammography system, as indicated at step 102. As one example, the one or more images can be provided by retrieving the images from data storage. In another example, the one or more images can be provided by acquiring the one or more images using a mammography system.

Figure 6:
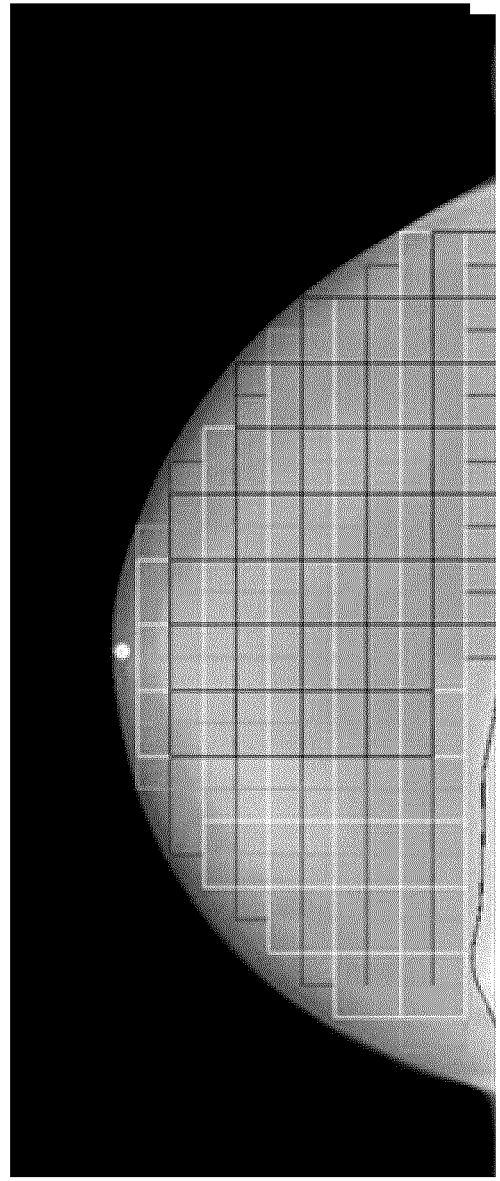
FIG. 6 is an example of a grid-like pattern of overlapping regions-of-interest for which imaging biomarkers can be computed

The one or more images are processed to generate the desired imaging biomarker after the images have been provided. First, one or more ROIs are selected in each image to be processed, as indicated at step 104. The ROIs may be of any reasonable shape or size (e.g., 32×32 pixels, 256×256 pixels), and in some instances can be selected to be at least partially overlapping to provide more points of measurement. In some embodiments, multiple ROIs could be arranged such that at least some of the ROIs form a pattern of overlapping ROIs, an example of which is illustrated in FIG. 6.

Then, a task-based measure that estimates the SNR of a detection task in a given ROI is computed, as indicated at step 106. In some embodiments, the task-based measure is based on a "model observer," which is an algorithmic construct that evaluates an imaging task. Examples of model observers can include pre-whitening, non-prewhitening, Hotelling, and channelized Hotelling model observers. The model observers can be modified to include "human" parameters that account for human visual response, decision making, and skill.

As one example, the task-based measure can be computed according to Eqn. (4). Using this approach, information about a resolution-based measure of the imaging system, which may be the PSF or the MTF, T(u,v), of the mammography system, is provided; one or more task functions, W(u,v), are selected or otherwise computed; and an noise-based measure of the image is computed. The detection task can be selected or otherwise computed based on any suitable combination of lesion size, shape, composition, or combinations thereof. The noise-based measure of the image can include normalized noise power spectrum or a noise covariance matrix, which are extracted from or estimated for the given ROI.

The step of computing the task-based measure can be repeated for any number of the ROIs, and can include computing the task-based measure for the same ROI using different task functions, computing the task-based measure for different ROIs using the same or different task functions, or combinations thereof.

Lastly, a report of the imaging biomarker can be generated based on the computed task-based measures, as indicated at step 108. As one example, an image, or "map," of the imaging biomarker can be generated by proportionally assigning colormap values based on values of the task-based measure. For instance, the colormap can be a gray scale map or other suitable colormap. The imaging biomarker may indicate potential lesion conspicuity, the relative ease of potential lesion detection, or the degree of potential lesion masking expected at each location. In these examples, the map can be displayed as a semi-transparent overlay, or as a side-by-side comparison, to the original mammographic image.

In some embodiments, the imaging biomarker is the $d_{local}$ parameter described above, in which case lower values of $d_{local}$ correspond to higher probabilities that a potential lesion in the region with low $d_{local}$ values will not be detected. Accordingly, the generated report may be a $d_{local}$ map, in which darker image intensity values correspond to regions where it will be more difficult to detect a lesion that may be present in those regions.

The imaging biomarker can also be expressed as a masking index that provides a quantitative measure of regions that are "masked" and regions that are "not masked." An indication that a region is "masked" can be expressed on one or more intermediate outputs. One example of an intermediate output is an average value of the $d_{local}$ parameter across the mammographic image. In some instances, an intermediate output is a based on calculations in a quadrant (e.g., an upper outer quadrant, an upper inner quadrant, a lower outer quadrant, a lower inner quadrant). Examples of calculations that can be made for a given quadrant include a detectability value for each quadrant, a weighted average detectability value for each quadrant, or an indication of which quadrant in a particular mammographic image is the "worst" quadrant (e.g., the quadrant having the lowest average $d_{local}$ value). Another example of an intermediate output includes the calculated percent area of regions in a mammographic image that are identified as "bad" relative to a defined threshold value for local detectability, $d_{local}$. The standard deviation and other statistical measures of detectability can also be used as intermediate outputs. These intermediate outputs can be combined in any number of combinations to provide a "masking index" that can be reported as the imaging biomarker.

In some other embodiments, the imaging biomarker may be expressed on a relative scale corresponding to the probability of missing a lesion if it was present, or based on an odds ratio ("OR"). In still other embodiments, the imaging biomarker can indicate the lesion detectability rather than lesion conspicuity. In such embodiments, the imaging biomarker can be expressed on a relative scale corresponding to the probability of finding a lesion.

The imaging biomarker can also be based on secondary measures of masking, which may include the fractional area of high masking probability, overall masking probability, and heterogeneity of masking probability in the image. As still another example, the imaging biomarker may also include re-expressing the masking measure of lesion conspicuity as a percentage risk of missing a lesion, if calibrated to historical miss-rates of lesion detection, or as a BIRADS-equivalent scale measure.

Generating the imaging biomarkers may also include calculating other parameters, such as texture parameters that can be extracted from the mammographic images. Examples of texture parameters include fractal dimension, the shape of the power spectrum of the ROIs of the image, and the β parameter described above. Generating the imaging biomarkers may also include extracting the volumetric breast density and the breast thickness as a function of position on the image. The texture parameters, the VBD, and breast thickness can be extracted from the original images, or from log-normalized images.

Generating the imaging biomarkers may also include using a system model of the x-ray imaging signal propagation to reduce measurement variability, as described above. For instance, the system model can be based on parameters extracted from the DICOM header, from tables of system performance, and other measurements of image quality. The x-ray imaging system model may incorporate a monoenergetic or polyenergetic model of the x-ray spectrum, and can include various physical phenomena such as x-ray scatter, detection absorption probabilities, and transmission probabilities through the breast tissue, transmission ratios through the anti-scatter grid, detector response blurring, and electronic noise. When an x-ray imaging system model is used, the method for generating the imaging biomarker may include computing a scale factor based on the model to adjust values to correspond to the actual ROI. As an example, the scale factor may include the scale factor described in Eqn. (10).

In all of these embodiments, the generated report can include maps of the imaging biomarker, or other forms of displaying information related to or based on the imaging biomarker, including textual displays.

Figure 2:
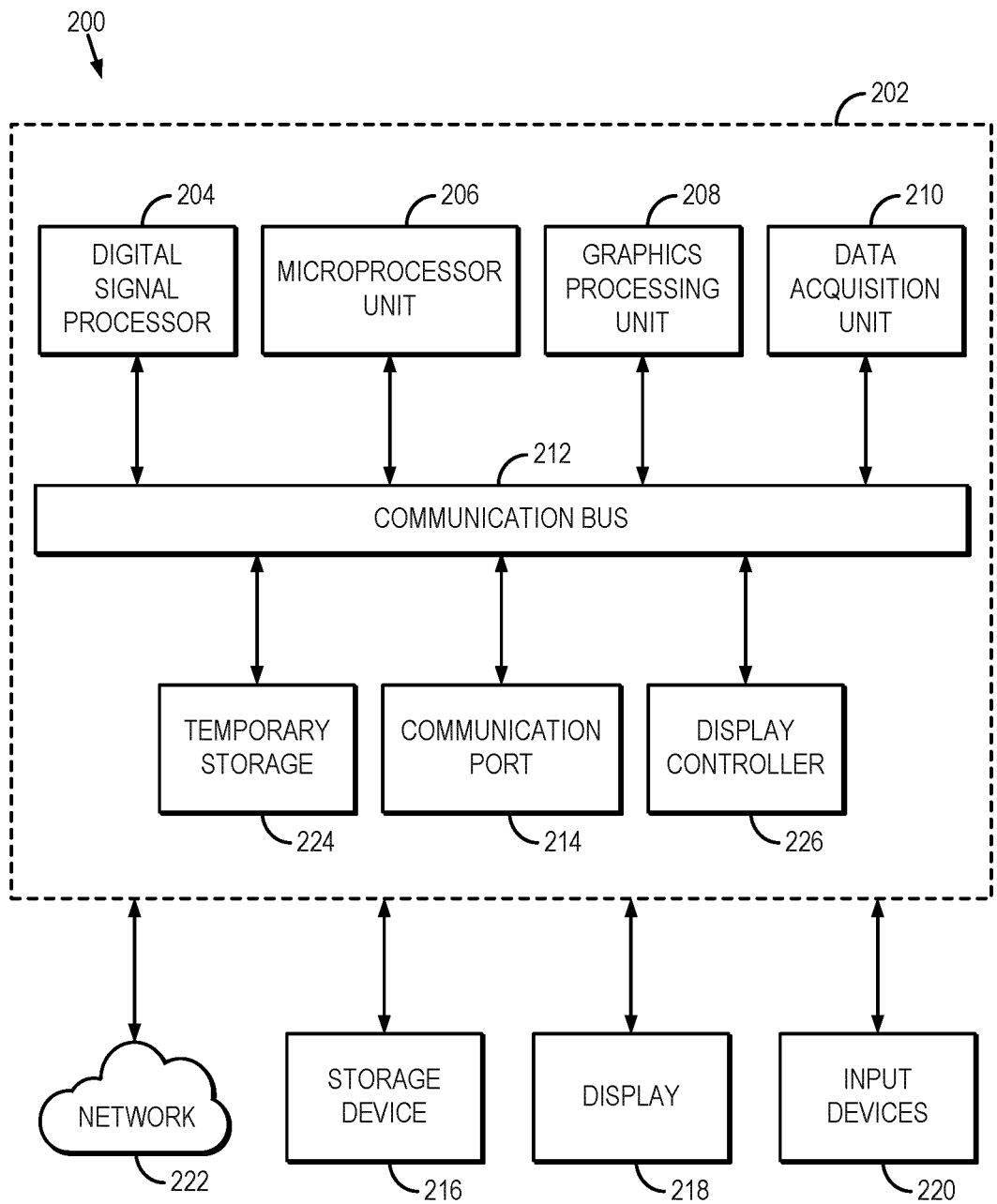
FIG. 2 is a block diagram of an example computer system that can implement the method of FIG. 1.
Figures 3A, 3B:
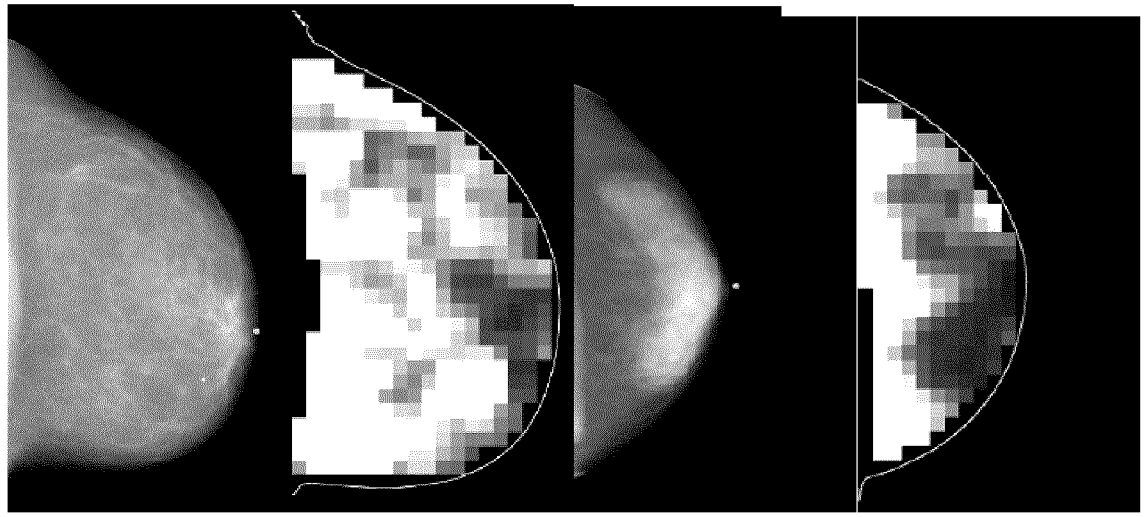
FIGS. 3A-3D illustrates examples of mammographic images and their corresponding $d_{local}$ maps, which indicate lesion detectability or conspicuity.
Figures 3C, 3D:
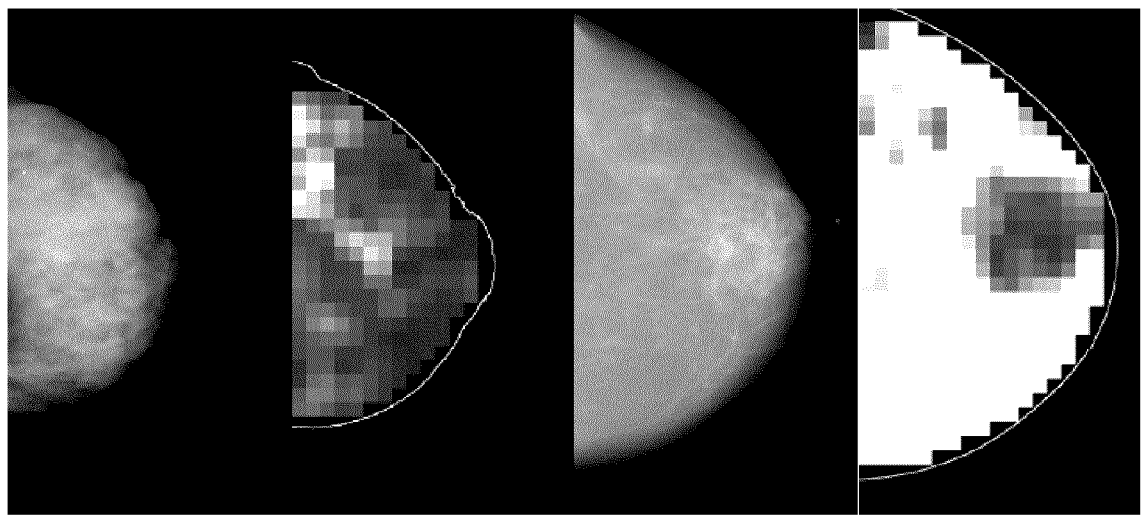

Referring now to FIG. 2, a block diagram of an example computer system 200 that can be configured to generate an image biomarker that indicates a degree of lesion detectability based on one or more mammographic images acquired from a subject, as described above, is illustrated. The one or more mammographic images can be provided to the computer system 200 from an x-ray imaging system, such as a mammography system, or from a data storage device, and are received in a processing unit 202.

In some embodiments, the processing unit 202 can include one or more processors. As an example, the processing unit 202 may include one or more of a digital signal processor ("DSP") 204, a microprocessor unit ("MPU") 206, and a graphics processing unit ("GPU") 208. The processing unit 202 can also include a data acquisition unit 210 that is configured to electronically receive data to be processed, which may include mammographic images. The DSP 204, MPU 206, GPU 208, and data acquisition unit 210 are all coupled to a communication bus 212. As an example, the communication bus 212 can be a group of wires, or a hardwire used for switching data between the peripherals or between any component in the processing unit 202.

The DSP 204 can be configured to receive and processes the mammographic images. The MPU 206 and GPU 208 can also be configured to process the mammographic images in conjunction with the DSP 204. As an example, the MPU 206 can be configured to control the operation of components in the processing unit 202 and can include instructions to perform processing of the mammographic images on the DSP 204. Also as an example, the GPU 208 can process image graphics.

In some embodiments, the DSP 204 can be configured to process the mammographic images received by the processing unit 202 in accordance with the algorithms described herein. Thus, the DSP 204 can be configured to generate task-based measures of the SNR of a detection task, to generate imaging biomarkers based on those task-based measures, and so on.

The processing unit 202 preferably includes a communication port 214 in electronic communication with other devices, which may include a storage device 216, a display 218, and one or more input devices 220. Examples of an input device 220 include, but are not limited to, a keyboard, a mouse, and a touch screen through which a user can provide an input.

The storage device 216 is configured to store mammographic images, whether provided to or processed by the processing unit 202, and maps based on the imaging biomarkers, such as lesion conspicuity or lesion detectability maps. The display 218 is used to display images, such as images and maps that may be stored in the storage device 216, and other information. Thus, in some embodiments, the storage device 216 and the display 218 can be used for displaying the imaging biomarker maps, and for outputting other information such as data plots or other reports based on statistical measures or other information computed, derived, or extracted from the mammographic images or imaging biomarkers.

The processing unit 202 can also be in electronic communication with a network 222 to transmit and receive data, including mammographic images and other information. The communication port 214 can also be coupled to the processing unit 202 through a switched central resource, for example the communication bus 212.

The processing unit 202 can also include a temporary storage 224 and a display controller 226. As an example, the temporary storage 224 can store temporary information. For instance, the temporary storage 224 can be a random access memory.

Example 1: A Quantitative Measure of Radiographic Masking by Dense Tissue in Mammography The detection sensitivity of screening mammography is reduced for dense breasts where the appearance of fibroglandular tissue can mask suspicious lesions. In this example, a measure of the degree of masking expected for a mammographic image is computed, as described above. This masking measure can be useful for informing the decision to direct some women to supplemental imaging procedures not affected by density.

In the example described below, an adaptation of a model observer is used to estimate the detection task SNR, $d_{local}$, of a lesion embedded in various portions of the breast to indicate the level of detection difficulty.

Results

De-identified mammograms (n=138) were selected from a previous study for processing and analysis. The images were acquired on a GE Senographe 2000D (GE Healthcare, Chalfont St. Giles, UK). DICOM for-processing images were used for the density calculation and the subsequent $d_{local}$ calculation. FIGS. 3A-3D show examples of mammograms (left-hand side) and the corresponding $d_{local}$ maps (right-hand side) generated using Eqn. (4). Darker regions of the $d_{local}$ map correspond to regions where it is expected to be more difficult to detect lesions. In general, these darker areas correspond to areas of increased density, although texture clearly plays a role in decreasing detectability as well.

Figure 4A:
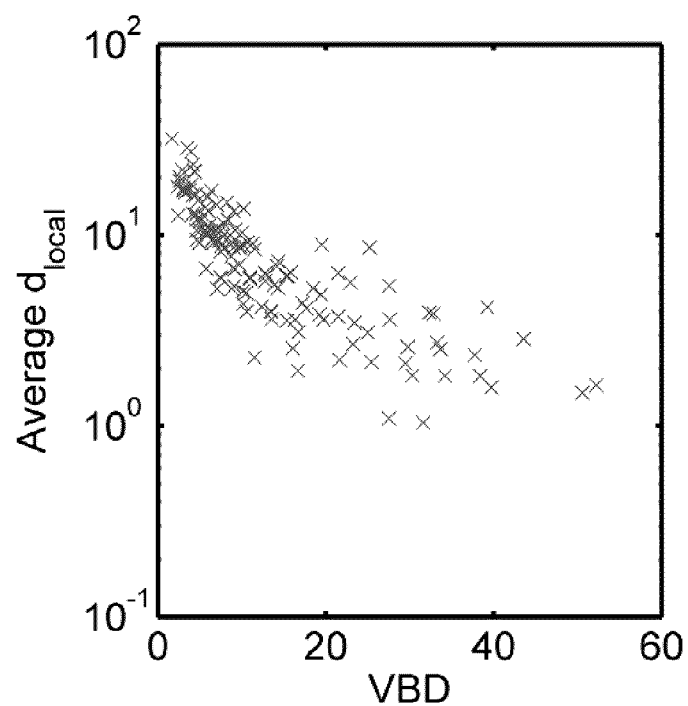
FIGS. 4A and 4B illustrate example plots of average $d_{local}$ values versus volumetric breast density (FIG. 4A) and inverse power-law coefficient, $\beta$ (FIG. 4B)
Figure 4B:
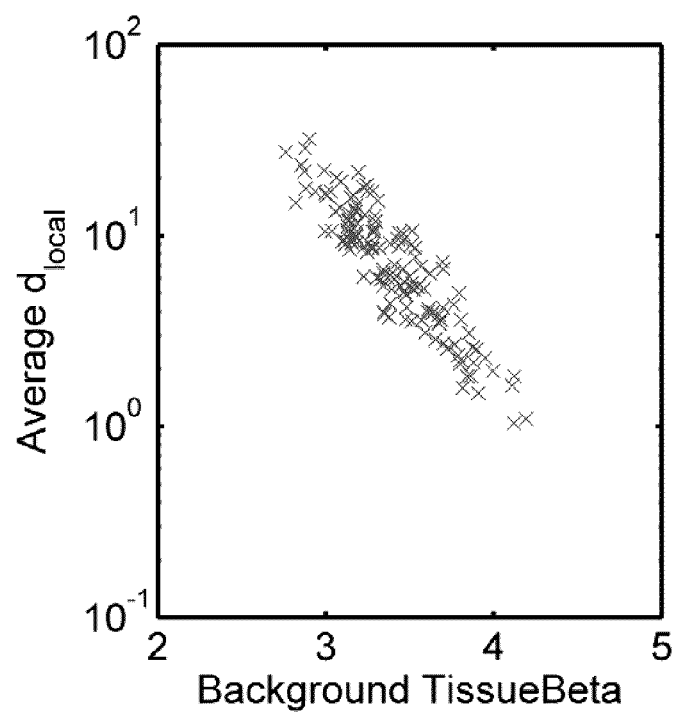

FIG. 4A shows the average $d_{local}$ plotted against the volumetric breast density measured using a volumetric density algorithm, Cumulus V. There is evidence of a trend with very large $d_{local}$ values for the fattiest breasts and decreasing for the highest density categories. The Pearson correlation between $\log_e (d_{local})$ and VBD was r=−0.82. The background texture appears to have a strong impact on $d_{local}$. As shown in FIG. 4B, there appears to be an almost linear relationship between $\log_e (d_{local})$ and β with a Pearson's correlation of r=−0.90.

Figure 5A:
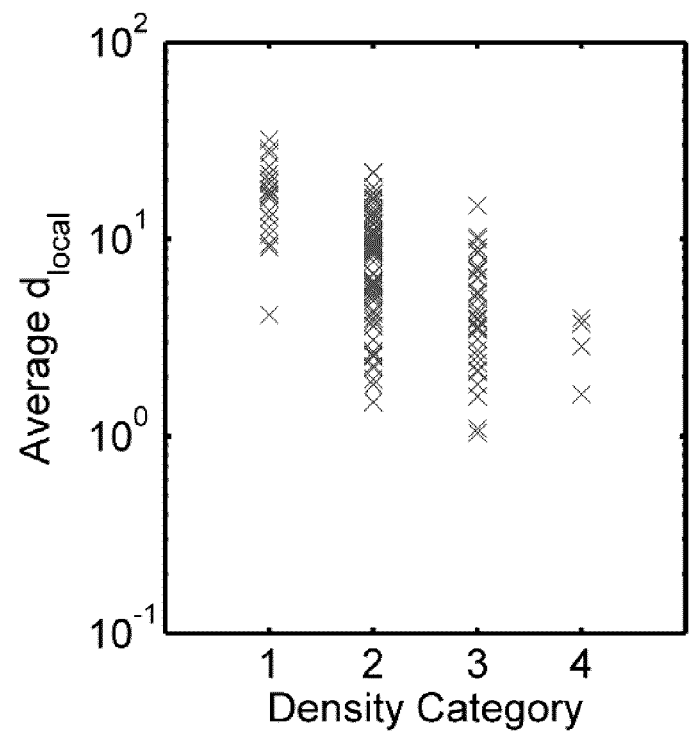
FIGS. 5A and 5B illustrate example plots of average $d_{local}$ values versus BIRADS density category (FIG. 5A) and fractional area of the breast that has $d_{local}$ values less than a threshold of 2.0 versus BIRADS density category (FIG. 5B)
Figure 5B:
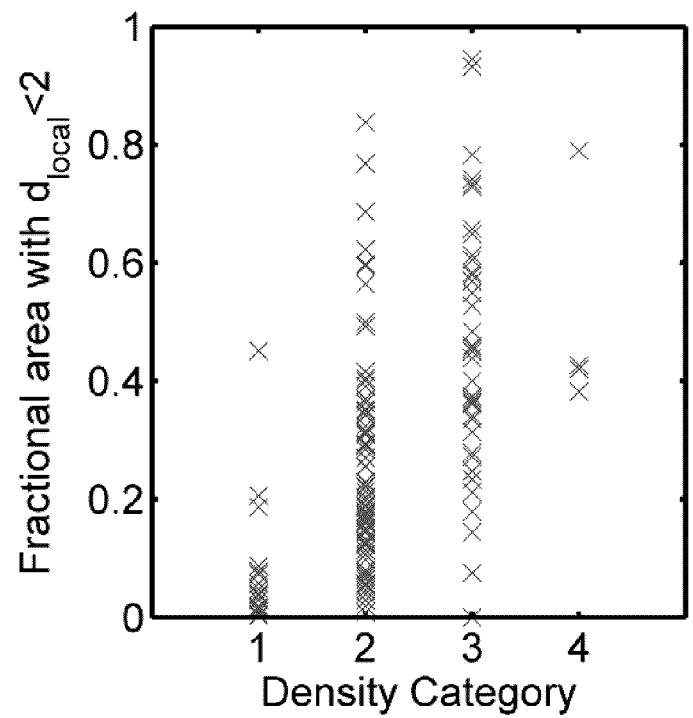

FIG. 5A shows the average $d_{local}$ for each radiologist-reported density category. The Spearman ranked correlation between $d_{local}$ and BIRADS category is ρ=−0.58. It is contemplated that the average $d_{local}$ is not likely to be a reliable indicator of the difficulty of the mammogram. In other words, mammograms with high average $d_{local}$ could still contain very difficult-to-read areas. To capture this effect, the fractional area of each mammogram that was below an arbitrary threshold of $d_{local}$=2 was also calculated and is presented in FIG. 5B. Here, the fattiest breasts have the smallest fractional areas with low $d_{local}$ and the densest breasts generally contain much higher fractions with this characteristic. The ranked correlation between $d_{local}$ and BIRADS category is ρ=0.61.

Example 2: Masking Study

In this study, the volumetric breast density ("VBD") and mean detectability, $\bar{d}_L$ (which is inversely related to the masking probability) were computed on the images of 78 women, of whom 26 had cancer. The same images were reviewed by two radiologists who independently rated the difficulty of finding cancer; the BIRADS density category (5th edition); and the diagnosis (negative/certainly benign to certainly malignant).

The detectability was computed at a constant contrast, ignoring variations in breast density. Thus, the calculation of $\bar{d}_L$, which is also referred to above as the $d_{local}$ parameter, had no direct dependence with the VBD estimate.

Figure 7A:
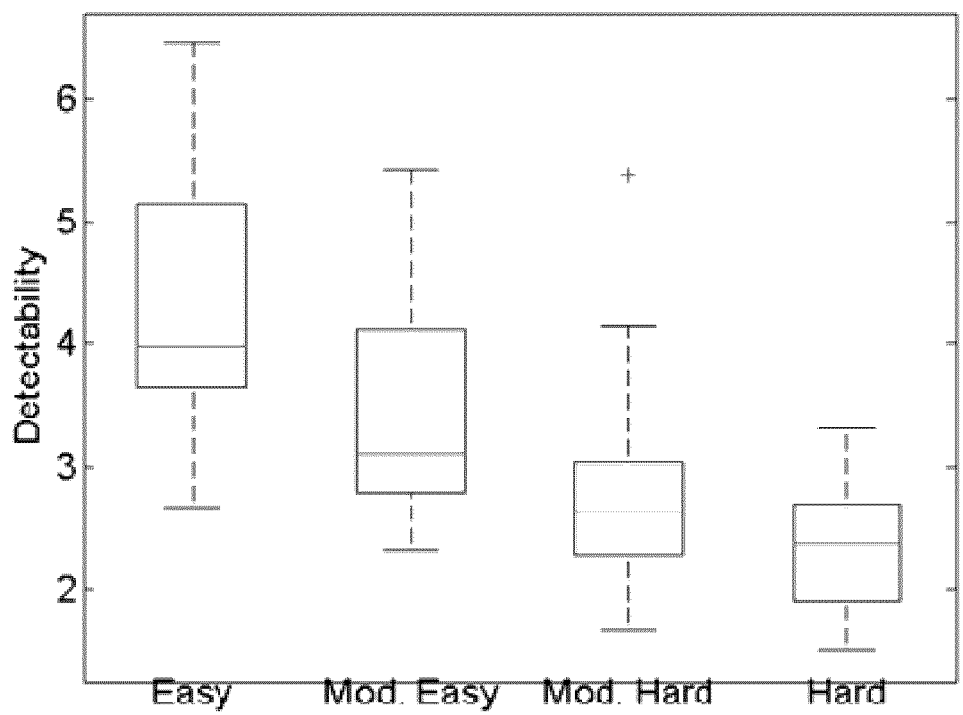
FIGS. 7A and 7B illustrate example boxplot representations of detectability versus difficulty of detection (FIG. 7A) and detectability versus BIRADS density (FIG. 7B) for two independent readers, in these figures the boxes, line, whiskers, and individual points represent the interquartile range ("IQR"), median, 1.5 times the IQR, and the remaining data points, respectively.
Figure 7B:
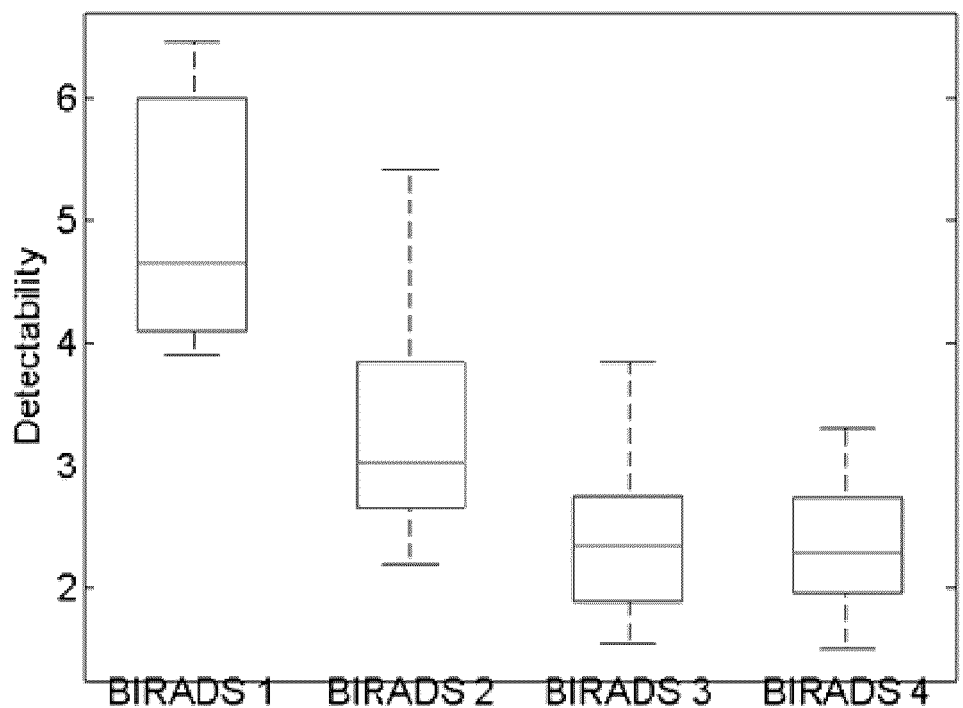

The VBD and $\bar{d}_L$ metric had similar correlations with difficulty and BIRADS. For one reader, VBD had a stronger correlation and for the other (the more experienced radiologist), $\bar{d}_L$ had a stronger correlation. When combining both readers' ratings, VBD was determined to be the slightly better metric (see Table 1 below). The 95% confidence interval for the coefficients (not shown) was computed, and the differences were not found to be statistically significant (i.e., the correlations were effectively equivalent). This is in part due to the subjectivity and coarse categorization of the difficulty and BIRADS density ratings. FIGS. 7A and 7B show boxplots of the detectability, $\bar{d}_L$, versus difficulty and BIRADS density.

TABLE 1

Pearson correlation coefficient between detectability and VBD versus difficulty and BIRADS density. None of these differences in the absolute correlation between d' and VBD were found to be statistically significant.

|  | $\bar{d}_L$ vs. difficulty | VBD vs. difficulty | $\bar{d}_L$ vs. BIRADS | VBD vs. BIRADS |
|---|---|---|---|---|
| Reader 1 | −0.49 | 0.56 | −0.56 | 0.68 |
| Reader 2 | −0.63 | 0.57 | −0.60 | 0.59 |
| Combined | −0.57 | 0.54 | −0.57 | 0.63 |

Figure 8A:
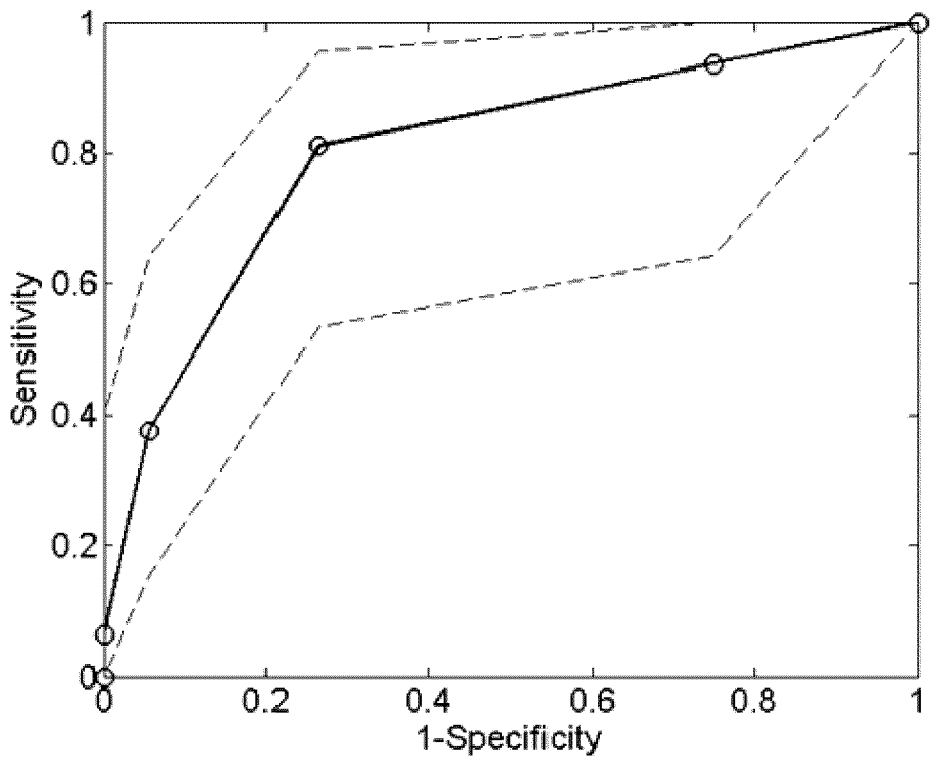
FIGS. 8A and 8B illustrate example receiver-operator characteristics ("ROC") curves for a lower category of detectability (FIG. 8A) and an upper category of detectability (FIG. 8B), in these figures the bottom and upper dotted lines represent the 95% confidence interval in the sensitivity (the confidence interval in the false positive fraction (1-specificity) is not illustrated).
Figure 8B:
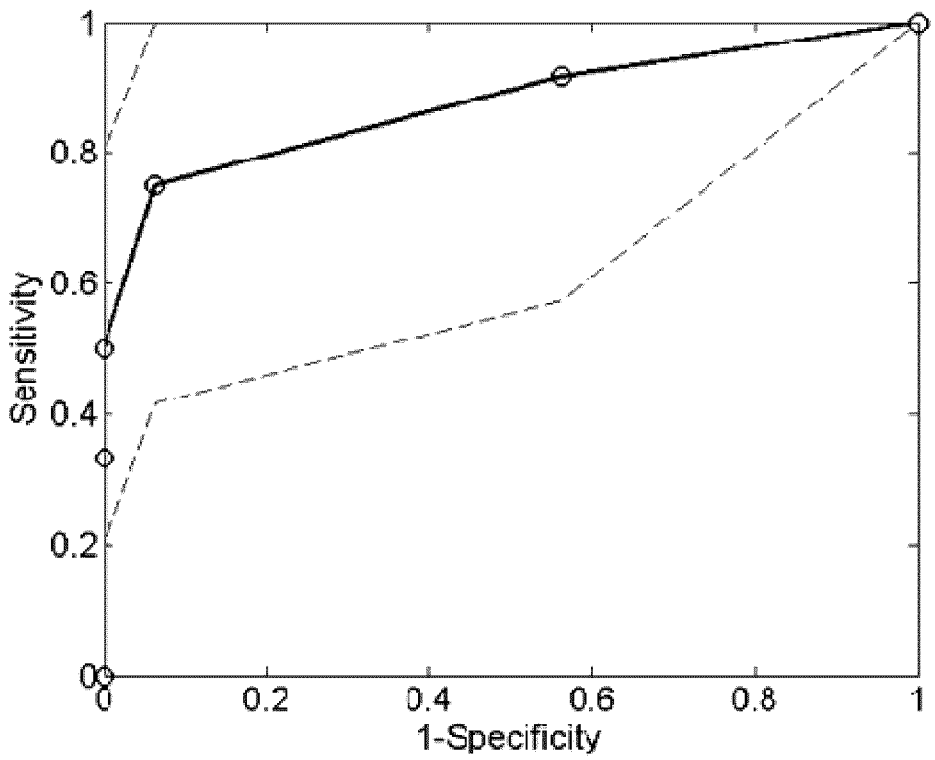

A receiver-operator characteristics (ROC) analysis was also performed in order to determine whether changes in VBD, $\bar{d}_L$, and BIRADS density were linked to changes in radiologists' performance in detecting cancer. For this analysis, the DCIS cancer cases (12 in total) were excluded since the detections of calcifications are generally not affected by density and/or masking. The threshold $\bar{d}_L$ and VBD values were determined so that they optimized the discrimination between the readers' BIRADS 1-2 and BIRADS 3-4 ratings. FIGS. 8A and 8B show the ROC curves for the two categories of detectability. Table 2 shows the percent accuracy of the observers versus $\bar{d}_L$, VBD, and BIRADS density. There was an increase (not significant) in accuracy when increasing detectability (i.e., decreased masking), whereas there was no such change when increasing VBD. Moreover, a statistically significant increase in specificity was observed with increasing $\bar{d}_L$ at the clinically-relevant operating point on the ROC curve. The change in specificity when changing VBD at that same operating point was not statistically significant (see Table 2 below). The changes in accuracy and specificity vs. BIRADS density are similar to the changes in accuracy and specificity versus $\bar{d}_L$.

TABLE 2

Patient count (for both readers) and the percent accuracy (AUC) and specificity at the lower and upper categories of detectability, VBD, and BIRADS. The 95% confidence interval is shown in brackets. Italicized values are statistically significant.

|  | High $\bar{d}_L$ | Low $\bar{d}_L$ | Low VBD | High VBD | BIRADS 1-2 | BIRADS 3-4 |
|---|---|---|---|---|---|---|
| Count | 22 | 44 | 30 | 36 | 36/23 | 30/43 |
| AUC | 88% | 80% | 83% | 83% | 89% | 77% |
|  | [66 97] | [63 90] | [61 94] | [64 93] | [72 96] | [51 90] |
| Specificity | 94% | 73% | 85% | 75% | 88% | 74% |
|  | [80 100] | [62 83] | [73 94] | [63 85] | [76 95] | [62 84] |

In summary, the masking score was found to have similar correlation coefficients with respect to the radiologists' (i.e., readers') impression of difficulty and to their BIRADS 5th edition categorization when compared to percent breast density. However, the masking score was found to behave similarly to BIRADS when looking at radiologists' (i.e. readers') performance, whereas percent breast density does not. These data suggest the masking score may represent a more objective measure where there is variability between and amongst radiologists due to subjective interpretations of the data. The masking score is anticipated to provide a more highly reproducible measure when compared to radiologist interpretation. Further, the masking score enables high sensitivity while reducing the number of false positives compared to VBD.

Systems and methods for evaluating the impact of density masking on lesion detectability have been described here. Initial investigations have suggested that this measure appears to be very sensitive to both fibroglandular density and texture. Such a tool may prove useful in helping to identify mammograms with a potential for limited observer SNR that need a more careful assessment, to help improve CAD algorithms, or as a quantitative measure to identify women who should be invited to be screened with alternative imaging modalities.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for generating an imaging biomarker that indicates a degree of lesion masking in a mammographic image obtained with an x-ray imaging system, the steps of the method comprising:
    (a) providing a mammographic image acquired with an x-ray imaging system;
    (b) processing the mammographic image to estimate a task-based measure that is based on a statistical measure of a detection task;
    (c) generating an imaging biomarker that indicates a degree of lesion masking in mammographic image based on the estimated task-based measure; and
    (d) generating a report that indicates the degree of lesion masking in the mammographic image based on the generated imaging biomarker.

2. The method as recited in claim 1, wherein step (b) includes selecting a region-of-interest (ROI) in the mammographic image and estimating the task-based measure for the selected ROI.

3. The method as recited in claim 2, wherein step (b) is repeated to select a plurality of ROIs in the mammographic image.

4. The method as recited in claim 3, wherein at least some of the plurality of ROIs are arranged to be overlapping with others of the plurality of ROIs.

5. The method as recited in claim 2, wherein the task-based measure is based on a signal-to-noise ratio (SNR) of the detection task.

6. The method as recited in claim 5, wherein the task-based measure is estimated using a model observer.

7. The method as recited in claim 6, wherein the model observer is at least one of a pre-whitening model observer, a non-pre-whitening model observer, a Hotelling model observer, or a channelized Hotelling model observer.

8. The method as recited in claim 6, wherein the model observer is a modified model observer that accounts for at least one of human visual response, human decision making, or human skill.

9. The method as recited in claim 6, wherein the task-based measure is based on a resolution-based measure of the x-ray imaging system, a task function that describes the detection task, and a noise-based measure that is estimated for the ROI.

10. The method as recited in claim 9, wherein the resolution-based measure is at least one of a point spread function and a modulation transfer function.

11. The method as recited in claim 9, wherein the noise-based measure is at least one of a normalized noise power spectrum or a noise covariance matrix.

12. The method as recited in claim 9, wherein the noise-based measure is estimated based on image intensity values in the ROI.

13. The method as recited in claim 9, wherein the noise-based measure is estimated based on a system model of x-ray propagation.

14. The method as recited in claim 9, wherein the task function describes a detection of a lesion having at least one of a selected size, a selected shape, or a selected composition.

15. The method as recited in claim 1, wherein the generated imaging biomarker indicates a degree of difficulty for the detection task to detect whether lesion may be present in the mammographic image without identifying a presence of lesions in the mammographic image.

16. The method as recited in claim 1, wherein the generated imaging biomarker indicates a probability of missing a detection of a lesion.

17. The method as recited in claim 1, wherein generating the imaging biomarker includes computing a secondary measure of conspicuity of lesions that may be present in the mammographic image.

18. The method as recited in claim 17, wherein the secondary measure of conspicuity of lesions includes at least one of fractional area of increased lesion masking probability, overall lesion masking probability, or heterogeneity of lesion masking probability in the mammographic image.

19. The method as recited in claim 1, wherein generating the imaging biomarker includes computing a percentage risk of missing a detection of a lesion.

20. The method as recited in claim 1, wherein generating the imaging biomarker includes re-expressing the task-based measure as a breast imaging-reporting and data systems (BIRADS) equivalent scale measure.

21. The method as recited in claim 1, wherein the report generated in step (d) includes a map that relates values of the imaging biomarker to a colormap.

22. The method as recited in claim 1, further comprising providing the generated imaging biomarker to a computer-aided detection system.

23. The method as recited in claim 1, wherein the detection task indicates the detectability of lesions that may be present in the mammographic image by modeling the lesions that may be present in the mammographic image as at least one of a disk, a Gaussian profile blob, a synthetic spiculated breast cancer lesion, a single microcalcification, or a cluster of microcalcifications.

24. The method as recited in claim 1, wherein the x-ray imaging system is at least one of a digital mammography system, a digital tomosynthesis system, or a dual-energy mammography system.

25. The method as recited in claim 1, wherein step (c) includes calculating an average local detectability value across the mammographic image.

26. The method as recited in claim 1, wherein step (c) includes calculating a local detectability value for each quadrant of the mammographic image.

27. The method as recited in claim 1, wherein step (c) includes calculating a weighted average local detectability value for each quadrant.

28. The method as recited in claim 1, wherein step (c) includes calculating a local detectability value for each quadrant of the mammographic image and identifying the quadrant of the mammographic image having the lowest local detectability value.

29. The method as recited in claim 1, wherein step (c) includes calculating a local detectability value at each voxel location in the mammographic image and calculating a percent area of the mammographic image associated with local detectability values that are below a threshold value.

* * * * *